United States Patent [19]
Crivello

[11] Patent Number: 6,069,259
[45] Date of Patent: May 30, 2000

[54] MULTIFUNCTIONAL POLYMERIZIBLE ALKOXY SILOXANE OLIGOMERS

[75] Inventor: James Vincent Crivello, Clifton Park, N.Y.

[73] Assignee: Rensselaer Polytechnic Institute, Troy, N.Y.

[21] Appl. No.: 09/019,632

[22] Filed: Feb. 6, 1998

[51] Int. Cl.[7] .............................. C07D 303/02; C07F 7/02
[52] U.S. Cl. .................... 549/214; 549/215; 556/458; 556/460; 556/467; 528/27; 528/28; 528/32; 528/33; 528/41
[58] Field of Search .................................. 556/458, 460, 556/467; 528/27, 32, 33, 41; 549/214, 215

[56] References Cited

U.S. PATENT DOCUMENTS 5,019,607  5/1991  Coltrain et al. ..................... 523/435
5,316,695  5/1994  Wilkes et al. ....................... 252/315.6

FOREIGN PATENT DOCUMENTS 94113136  8/1994  European Pat. Off. .

OTHER PUBLICATIONS

Crivello, J., & Mao, Z., "Synthesis of Novel Multifunctional Siloxane Oligomers using Sol–Gel Techniques and Their Photoinitiated Cationic Polymerization," Chem. Mater., vol. 9, pp. 1554–1561, 1997.

Crivello, J., & Mao, Z., "Preparation and Cationic Photopolymerization of Organic–Inorganic Hybrid Matrixes," Chem. Mater., vol. 9, pp. 1562–1569, 1997.

Crivello, J., Yang, B. & Whan–Gi, K., "Synthesis and Electron–Beam Polymerization of 1–Propenyl Ether Functional Siloxanes," Pure Appl. Chem., vol. A33(4), pp. 399–415, 1996.

Crivello, J., & Löhden, G., "Synthesis and Photopolymerization of 1–Propenyl Ether Functional Siloxanes," Chem. Mater., vol. 8, pp. 209–218, 1996.

*Primary Examiner*—Porfirio Nazario-Gonzalez
*Attorney, Agent, or Firm*—Heslin & Rothenberg, P.C.

[57] ABSTRACT

A composition relating to an oligomeric alkoxy siloxane substituted with polymerizible epoxy or 1-alkenyl groups, and a process for the production of that composition, are disclosed. The process entails a hydrolysis-condensation oligomerization of an epoxy- or 1-alkenyl ether-functional trialkoxy silane, catalyzed by an ion exchange resin, and separation of the resin from the resulting oligomer.

18 Claims, No Drawings

MULTIFUNCTIONAL POLYMERIZIBLE ALKOXY SILOXANE OLIGOMERS

FIELD OF THE INVENTION

The invention relates to alkoxy siloxane oligomers.

BACKGROUND OF THE INVENTION

Multifunctional monomers are customarily incorporated in polymers at low levels in order to provide for crosslinking of the polymer. At high levels, however, polymerization of multifunctional monomers characteristically proceeds only to low conversions due to trapping of residual reactive functionality within the rigid, crosslinked network as it is formed. Preparation of epoxy functional and 1-propenyl ether functional methyl siloxanes has been described by applicant. These oligomers undergo rapid thermally induced and photoinduced cationic polymerization and proceed to high conversions. The anomalous behavior in the case of the siloxane-containing monomers has been attributed to the conformational flexibility of the siloxane (Si—O—Si) bond and to free volume effects.

Preparation of similar multifunctional alkoxy siloxanes is difficult to accomplish by prior art methods. Epoxy-functional trialkoxy silanes employed as glass coupling agents to increase adhesion between epoxy matrices and reinforcing glass fibers are commercially available as starting materials. However, condensation polymerization of multifunctional alkoxy silanes generally results in a crosslinked gel.

Sol-gel techniques have been widely employed for the polymerization of alkoxy silanes, resulting in crosslinked glass-like matrices composed of Si—O—Si linkages. Typically, alkoxy silanes such as tetraethoxysilane (TEOS) are subjected to acid or base catalyzed hydrolysis-condensation in the presence of controlled amounts of water to yield a gel. In most acid catalyzed sol-gel processes, HCl is used, while NaOH and $NH_4OH$ are often employed as base catalysts.

However, while conventional sol-gel chemistry is convenient and easily carried out, it suffers from drawbacks which make it less attractive for the preparation of stable multi-functional oligomers. When sol-gel condensations are carried to completion, crosslinked matrices result. It is difficult to control the sol-gel reaction so that one can reproducibly make intermediate, soluble, low viscosity, fluid oligomers. When such materials are obtained, they exhibit poor pot-lives and gel on standing due to further condensation.

In addition, the basic hydrolysis catalysts used in the sol-gel reaction are strong inhibitors for cationic polymerizations, and it is difficult or impossible to remove conventional basic catalysts at the end of the reaction. Further, acid hydrolysis catalysts are not useful for the synthesis of epoxy-functional siloxanes since epoxy groups undergo spontaneous ring-opening reactions with acids.

There is therefore a need for a process for making pure multifunctional alkoxy siloxane oligomers reproducibly and in good yield. There is also a need for alkoxy siloxane oligomers that have long pot-lives and low viscosity.

SUMMARY OF THE INVENTION

In one aspect, the invention relates to a polymerizible alkoxy siloxane oligomer composition comprising the structure of Formula I:

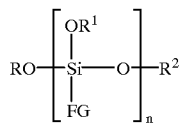

wherein R is an alkyl group of 1–10 carbons;

FG is a functional group and each FG in said oligomer is independently chosen from
- linear, branched and cyclic alkyl residues of 1 to 20 carbons terminating in a 1-alkenyl ether;
- linear, branched and cyclic alkyl ether residues of 1 to 20 carbons and 1 to 9 oxygens terminating in a 1-alkenyl ether;
- linear, branched and cyclic alkyl residues of 1 to 20 carbons terminating in an acrylate, an alpha-chloroacrylate, an alpha-cyanoacrylate or a methacrylate;
- linear, branched and cyclic alkyl ether residues of 1 to 20 carbons and 1 to 9 oxygens terminating in an acrylate, an alpha-chloroacrylate, an alpha-cyanoacrylate or a methacrylate;
- linear, branched and cyclic alkyl residues of 1 to 20 carbons substituted with an epoxide;
- linear, branched and cyclic alkyl ether residues of 1 to 20 carbons and 1 to 9 oxygens substituted with an epoxide;
- arylalkyl residues of 1 to 20 carbons substituted with an epoxide;
- arylalkyl ether residues of 1 to 20 carbons and 1 to 9 oxygens substituted with an epoxide; and
- epoxy-functional organosiloxane residues of 1 to 20 silicons and 1 to 20 carbons;

$R^1$ is R or

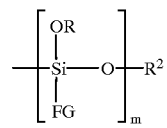

$R^2$ is R or

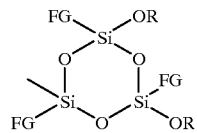

and m and n are independently 2 to 50.

In another aspect, the invention relates to a process for producing a polymerizible alkoxy siloxane oligomer comprising reacting one or more silane monomers of formula $(RO)_3Si\ FG$, wherein R is methyl or ethyl, and FG is an independently chosen radical substituted with an epoxy, 1-alkenyl, acrylate or methacrylate group as described above, with 0.5 to 2.5 equivalents of water in the presence of an ion exchange resin and separating the resin from the siloxane oligomer.

In yet another aspect, the invention relates to the polymerizible siloxane oligomers produced by reacting one or more alkoxy silane monomers of formula $(RO)_3Si\ FG$, wherein R is alkyl of 1–10 carbon S and FG is as described above, with 0.5 to 2.5 equivalents of water, in the presence of an ion exchange resin and separating the resin from the siloxane oligomer.

DETAILED DESCRIPTION OF THE INVENTION

The polymerizible siloxane oligomers of the invention have the structure of Formula I:

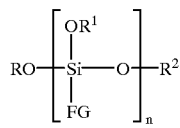

I wherein R is an alkyl group of 1–10 carbons;
$R^1$ is R or

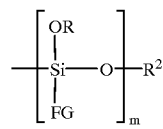

$R^2$ is R or

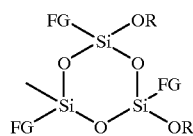

II m and n are independently 2 to 50; FG represents a functional group and each FG in the oligomer is independently chosen from radicals containing a polymerizable functional group other than a siloxane.

In the above formula, preferred alkoxy (RO) groups are methoxy or ethoxy. The polymerizible functional group FG is preferably a radical containing epoxy or 1-alkenyl functionality, for example aliphatic and aromatic epoxides, glycidyl ethers, vinyl ethers, 1-butenyl ethers, 1-propenyl ethers, although acrylates, methacrylates, alpha-cyanoacrylates, and alpha-chloroacrylates may also be used. Group FG may be one of the above radicals, or the oligomers may be substituted with two or more different functional groups by mixing monomers in the oligomerization reaction. More preferably group FG has a structure chosen from Formulae A–P, or there may be two or more different groups FG chosen from the same group of the structures. Most preferably, group FG is 2-(3,4-epoxycyclohexylethyl)(B) or 3-glycidoxypropyl(A) or the oligomer may be substituted with both (A) and

A

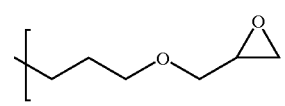

-continued

B

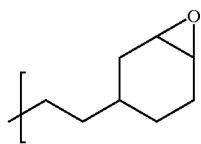

C

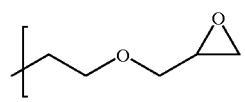

D

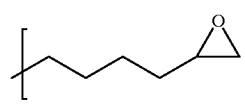

E

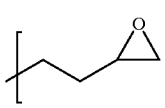

F

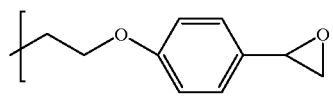

G

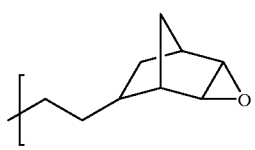

H

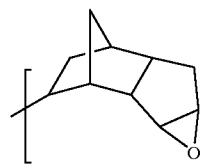

J

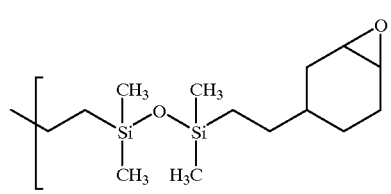

K

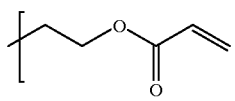

L

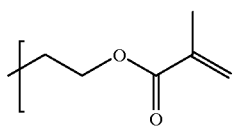

M

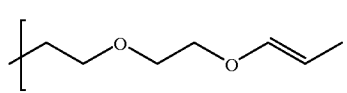

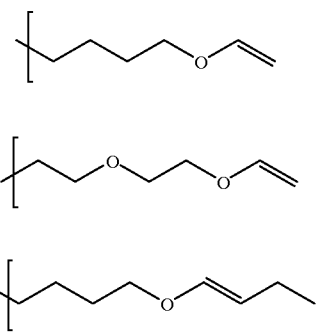

The siloxanes of the invention are straight- or branched-chain oligomers and may additionally contain one or more cyclic structures composed of three monomer units as end groups, as depict ed in Formula II. The presence of the ring structure is dependent on the number of equivalents of water employed in the reaction, and on reaction conditions, including temperature and time. The oligomer chains are composed of from two to fifty siloxane monomer units, preferably of from two to twenty monomer units.

Alkoxy siloxane oligomers, including the polymerizible siloxanes of the invention, may be synthesized by acid or base catalyzed hydrolysis and subsequent condensation of an alkoxy silane monomer of Formula $(RO)_3SiFG$, wherein R is alkyl and FG is a radical containing a polymerizable functional group. In the above formula, it is preferred that the alkoxy group (RO) is methoxy or ethoxy and that the functional group FG not be polymerizible by acids or bases at a rate comparable to that of the alkoxy siloxane. The polymerizible siloxanes of the invention are the product of the reaction when group FG is one or more of the epoxy- or 1-alkene-containing radicals described above in Formula I.

The hydrolys is-condensation reaction is catalyzed by an ion exchange resin in the form of a highly crosslinked bead which permits complete removal of the catalyst from the reaction mixture by filtration. Alternatively, the condensation may be carried out as a continuous process on a fixed bed of the resin. Removal of the catalyst prevents further reaction of the oligomer leading to crosslinking, and results in a product which retains its initial viscosity during storage. The oligomers of the invention possess good shelf stability, showing no increase in viscosity on standing for more than two months.

The rate and extent of the hydrolysis-condensation reaction are dependent on the strength of the catalyst used. Strong acids or bases cause fast hydrolysis and condensation of alkoxysilanes and high conversions to oligomers. The reaction is well controlled with ion exchange resins as catalysts. Condensation of the functionalized trialkoxysilanes in the presence of these catalysts proceeds at a convenient rate so that the reaction times are not inordinately long and at the same time slow enough that adequate control can be maintained over the reaction to provide reproducible molecular weight control and to avoid gelation.

Highly crosslinked styrene-divinyl benzene polymers with quaternary ammonium chloride or hydroxide, sulfonic acid, sodium sulfonate, or carboxylic acid functionality in the form of beads are well known in the art. Applicant has examined several commercially available resins containing quaternary ammonium functionality, differing in cross-link density, porosity, and ion exchange capacity, for their suitability in the process of the invention. Table 1 summarizes the results obtained with the three catalysts. All three ion exchange resins displayed similar catalytic activity in the condensation of 2-(3,4-epoxyclohexylethyl) trimethoxysilane. The results indicate that the chemical reaction is not limited by porosity or ion-exchange capacity of the resin. Exemplary styrene-divinyl benzene resins useful in the practice of the invention are Amberlyst® and Amberlite®, Rohm & Haas Company; Ionac®, Sybron Chemicals; Dowex®, Dow Chemical; NRW®, Purolite; Tulsion®, Thermax, Ltd; and the CG and SBG lines of resins from Resintech, Inc.

TABLE 1

|  | Amberlite A-27 | Amberlite IRA-400 | Amberlite IRA-904 |
|---|---|---|---|
| Conversion of Methoxy groups (%) | 82 | 80 | 78 |
| Type I Porosity % | Macroporous/ 51% | Gel | Macroporous/ 50% |
| Water (%) | 45 | — | 57 |
| Ion Exchange Capacity (mequiv/g) | 2.6 | 4.0 | 4.0 |

When sufficient water to hydrolyze all three alkoxy groups of the starting silane material is used, colorless, soluble, low-viscosity oligomers can be produced by the process of the invention. This suggests that the hydrolysis and condensation proceed in a discrete stepwise manner such that the rate of the reaction of the last of the three alkoxy groups is considerably slower than that of the other two.

The reaction is typically carried out in a solvent in which both the starting silane monomer and the siloxane product are soluble. Alcohols such as ethanol, t-butanol, n-propanol or isopropanol alone or in combination with water are preferred.

The reaction may be conducted at temperatures sufficient to maximize the rate of reaction while minimizing undesirable side reactions, generally from 0–100° C. and preferably from 35–70° C. At higher temperatures, the reaction is completed in a shorter time. For example, in a reaction conducted at 45 ° C., no starting material remained after 24 hours, while in a similar reaction carried out at 60° C., the reaction was completed in 12 hours. The extent of reaction may be determined by $^1$H NMR spectroscopy, by monitoring the consumption of methoxy groups (band centered at 3.45 ppm). Completion of the reaction occurs when approximately 80% of the alkoxy groups are converted to siloxane linkages.

The degree of condensation may be controlled by varying the ratio of water to trialkoxysilane present in the reaction mixture. Higher ratios of water result in an increase in the rate of the hydrolysis-condensation reaction and also in a greater proportion of oligomers with higher molecular weights. For example, the reaction was carried out at 60° C. with 1.0 and 1.5 equivalents of water, and 2-(3,4-epoxyclohexylethyl) trimethoxysilane as the starting material. For the reaction with 1.0 equivalents of water, the starting material was completely consumed in 12 hours, while for the reaction with 1.5 equivalents of water, the reaction was completed in only 9 hours. Equivalent ratios were calculated on the basis of the number of alkoxy groups per mole of starting trialkoxysilane (i.e., 3/mole). GPC analysis showed a broad distribution of oligomeric products in both cases, with a greater proportion of higher molecular weight material in reactions with 1.5 equivalents than in reactions with 0.5 equivalents of water.

In one embodiment of the invention, the viscosity of the oligomer may be from 100 to 1,000,000 cps. For many uses, oligomers having a viscosity of 500 cps to 5000 cps are preferred. In another embodiment, the reaction is carried to high molecular weight, and the oligomer which is isolated is a very high viscosity liquid or a glassy solid.

Epoxy, 1-alkenyl ether and vinyl ether compounds of the invention may be photopolymerized using UV or visible irradiation in the presence of diaryliodonium salt, triarylsulfonium salt and ferrocenium salt photoinitiators. The resin-photoinitiator mixtures may be also cured using e-beam irradiation. Acrylate and methacrylate oligomers may be photopolymerized using free radical initiators including benzoin, benzoin alkyl ethers, 1,1-diethoxy acetophenone, and 1-benzoylcyclohexanol as examples. Photopolymerization of an epoxy alkoxy siloxane oligomer is described in the examples.

The oligomers of the invention may also be polymerized thermally. Epoxy-functional siloxanes may be cured at elevated temperature using amine or anhydride curing agents known in the art, or diaryl iodonium salts. Polymerization of the siloxanes of the invention which contain a double bond, the 1-alkenyl ethers, vinyl ethers, and acrylates and methacrylates, may be initiated by azo or peroxide free radical initiators.

EXAMPLES

Example 1
Condensation of 2-(3,4-Epoxyclohexylethyl) trimethoxysilane (III)

A 50-ml round bottom flask fitted with a magnetic stirrer, a reflux condenser and a thermometer was charged with 1.97 grams (8 mmol) of III, 0.5–1.5 equivalents of deionized water, 80 mg of Amberlite IRA-904 ion exchange resin, and 0.5 of isopropanol. The colorless solution was stirred and heated at 60° C. Samples (0.5 g) of the reaction mixture were taken every several hours, cooled, filtered and the resulting colorless liquid combined with 0.5 grams of isopropanol and subjected to GPC and analysis. After 6 hours reaction, the reaction mixture contained mainly dimers, trimers and tetramers. Within the first 24 hours the reaction was essentially complete and thereafter little further reaction took place, as determined by GPC.

The solvent was removed under reduced pressure and the resulting colorless, viscous liquid oligomer was further characterized by $^1$H NMR spectroscopy and by RTIR analysis.

Example 2
Condensation of 3-Glycidoxypropyl trimethoxysilane (IV)

Into the same apparatus described above were added 1.89 grams (8.0 mmol) of IV, 1.5 equivalents (217 mg) of water, 80 mg of Amberlite IRA-904 ion exchange resin, and 0.5 grams of isopropanol. The colorless solution was stirred and heated at 60° C. Samples (0.5 g) of the reaction mixture were taken every several hours, cooled, filtered and the resulting colorless liquid combined with 0.5 grams of isopropanol and subjected to GPC and analysis. GPC analysis after 24 hours showed that product consisted primarily of octomers. The solvent was removed under reduced pressure and the resulting colorless liquid oligomer was further characterized by $^1$H NMR spectroscopy and by RTIR analysis.

Example 3
Synthesis of 1-(1-Propenoxy)-2-(2-trimethoxysilylethoxy) ethane (V)

A 100 ml round bottom flask fitted with a reflux condenser and a magnetic stirrer was charged with 8.8 grams (0.1 mol) of ethylene glycol monovinyl ether, 14.5 grams (0.12 mol) of allyl bromide, 4.8 grams (0–12 mol) of NaOH, 0.9 grams (3 mol %) of (n-Bu)$_4$NBr, and 20 ml of dried toluene. The white suspension was stirred and heated at 65 °C. for 12 hours. After cooling the reaction mixture, the resulting light yellow solution was separated from the white solids by decantation and washed with four times with 50 ml portions of water in a separatory funnel. Removal of the solvent under reduced pressure followed by vacuum distillation (b.p. 30° C./0.15 mm Hg gave the desired 1-allyloxy-2-vinyloxyethane as a colorless liquid.

The entire amount of 1-allyloxy-2-vinyloxyethane obtained in the above procedure was placed in a 50-ml round bottom flask fitted with a magnetic stirrer and reflux condenser and 3 mg of (PPh$_3$)$_3$RuCl$_2$ was added. The resulting light brown-purple solution was refluxed at 130° C. for 2.5 hours. Fractional vacuum distillation (b.p. 26° C./0.15 mm Hg) gave 1-(1-propenoxy) 2-vinyloxy ethane as a colorless liquid in an overall yield of 70% (9.17 g) from ethylene glycol monovinyl ether.

Into a 100 mL round bottom flask were added 9.17 grams (0.07 mol) of 1-(1-propenoxy)-2-vinyloxyethane, 3 mg of (PPh$_3$)$_3$RuCl$_2$, 11.3 grams of (MeO)$_3$SiH (0.09 mol), and 15 ml of dried toluene. The resulting purple solution was refluxed at 85° C. for 12 hours. Fractional vacuum distillation yielded 1-(1-propenoxy)-2(2-trimethoxysilylethoxy) ethane (V) in 36% yield as a colorless liquid, b.p. 70° C./0.15 mm Hg.

1-(1-Propenoxy)-2-(2-trimethoxysilylethoxy)ethane V was subjected to condensation in the presence of Amberlite IRA-904 ion exchange resin as described above. Condensation of V in the presence of 1 equivalent of water takes place very rapidly and is essentially complete after 1 hour of reaction at 60° C. At this point the reaction mixture consisted mainly of oligomers up to octomers with a small amount of residual monomer. Further reaction for up to 6 hours produced no further observable change by GPC. Integration of the $^1$H NMR spectrum of the reaction product after 1 hour reaction showed that the conversion of the methoxy groups had reached 58% (theoretical conversion 66.7%).

Example 4
Thin Film Polymerizations

Thin films (about 25 µm) of the liquid monomers containing 2.0 wt % of IOClO (4-n-decyloxyphenyl) phenyliodonium hexafluoroantimonate photoinitiator were drawn onto glass or steel panels and irradiated using a General Electric H3T-7 200 W medium pressure mercury arc lamp mounted at a distance of 12 cm from the sample. This apparatus was equipped with a mechanical shutter which could be opened to expose the samples to UV irradiation. Resins derived from examples 1–3 cured after an irradiation time of 1 second to give hard, transparent, colorless films.

Examples 5, 6, and 7

The 2-(3,4-epoxycyclohexylethyl)-substituted oligomer of Example 1 were cured thermally at by heating from 80° C. to 160° C. at 5° C./min., holding at 160° C. for 1 hour, then cooling to 80° C. at a rate of 5° C./min., using two levels of (4-(2'-hydroxyetradecyloxyphenyl) phenyliodonium hexafluoroantimonate, Sartomer Sarcat CD 1012, as the initiator. The physical properties of the resulting polymers were determined. Table 2 displays the curing data for oligomers of Example 1 and physical properties of the cured polymers as determined by differential scanning calorimetry.

TABLE 2

|  | Example 5 | Example 6 | Example 7 |
|---|---|---|---|
| Rxn Time (hr) | 12 | 12 | 23 |
| Initiator (%) | 1 | 1.5 | 1 |
| Peak (°C.) | 183 | 185 | 186 |
| Onset (°C.) | 175 | 175 | 180 |
| ΔH (J/g) | 300 | 326 | 273 |
| Storage Mod. (GPa/°C.) | 2.1/25 1.7/300 | — | 0.142/25 0.114/150 |
| Cure Volatiles (%/°C.) | 0.308/165 0.182/150 | — | 0.163/165 0.101/150 |
| TGA wt. loss (%/°C.) | 0.289/300 0.459/342 | — | 0.244/300 0.514/342 |
| CTE (ppm) | 74 | 68 | 68 |

The DSC data showing temperatures for the onset and peak of curing, and the enthalpy (ΔH) of curing indicates that the materials cure rapidly and completely. In addition, the siloxane oligomers of the invention possess unique thermomechanical properties when cured. The cured polymers show no glass transition at temperatures below 300 ° C. and have a relatively low coefficient of thermal expansion (CTE) between 0–180° C. The storage modulus of the polymers is very high, reflecting the high strength of the materials. In addition, the cured polymers are very stable at elevated temperatures, as indicated by low values for weight loss, (data from thermogravimetric analysis (TGA)) and very high values for the storage modulus at 300° C. These properties make the oligomers of the invention suitable for electronic applications, as composite materials, and for other applications requiring high mechanical strength, stability at high temperatures, and high rate of cure.

Example 8

Scale-up Synthesis

Placed in a 5 liter three necked flask equipped with a condenser, thermometer and a paddle stirrer were 600 g. 3,4-epoxycyclohexylethyl trimethoxysilane (Union Carbide A 186), 24.6 g. Amberlite IRA 904 ion exchange resin, 45 g. deionized water and 153 g. isopropanol. The reaction mixture was stirred and heated at 70° C. for 10 hours. After cooling, the reaction mixture was filtered through a sintered glass filter to remove the ion exchange resin. The solvents and excess starting material were removed on a rotary evaporator. A transparent, colorless oil , ~10,000 cps in viscosity, was produced in 87% yield.

The oligomer was combined with 1% IOC10 and irradiated using a General Electric H3T-7 medium pressure mercury arc lamp at a distance of 12 inches for 1 second. A hard glassy film resulted.

I claim:

1. A polymerizable siloxane oligomer comprising the structure of Formula I:

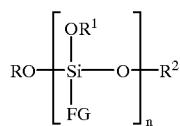

I wherein R is an alkyl group of 1–10 carbons;
FG is a functional group and each FG in said oligomer is independently chosen from
linear, branched and cyclic alkyl residues of 1 to 20 carbons terminating in a 1-alkenyl ether;
linear, branched and cyclic alkyl ether residues of 1 to 20 carbons and 1 to 9 oxygens terminating in a 1-alkenyl ether;
linear, branched and cyclic alkyl residues of 1 to 20 carbons terminating in an acrylate, an alpha-chloroacrylate, an alpha-cyanoacrylate or a methacrylate;
linear, branched and cyclic alkyl ether residues of 1 to 20 carbons and 1 to 9 oxygens terminating in an acrylate, an alpha-chloroacrylate, an alpha-cyanoacrylate or a methacrylate;
linear, branched and cyclic alkyl residues of 1 to 20 carbons substituted with an epoxide;
linear, branched and cyclic alkyl ether residues of 1 to 20 carbons and 1 to 9 oxygens substituted with an epoxide;
arylalkyl residues of 1 to 20 carbons substituted with an epoxide;
arylalkyl ether residues of 1 to 20 carbons and 1 to 9 oxygens substituted with an epoxide; and
epoxy-functional organosiloxane residues of 1 to 20 silicons and 1 to 20 carbons;

$R^1$ is R or

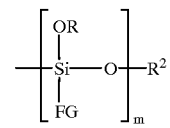

$R^2$ is R or

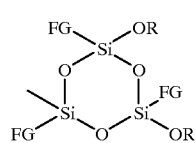

II and m and n are independently 2 to 50.

2. The composition of claim 1, wherein each FG has a structure independently chosen from the group consisting of the structures of Formulae A–P.

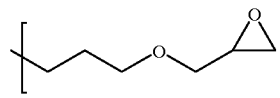

A

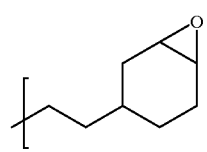

B

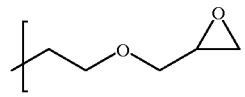

C

3. The composition of claim 1, wherein each FG is independently 2-(3,4-epoxycyclohexylethyl), 3-glycidoxypropyl, or 1-propenoxy-2-ethoxy ethyl.

4. The composition of claim 1, wherein each FG is independently 2-(3,4-epoxycyclohexylethyl) or 3-glycidoxypropyl.

5. The composition of claim 1, wherein m and n are independently 2 to 20.

6. A process for preparing a polymerizible alkoxy siloxane oligomer comprising reacting one or more silane monomers of formula $(RO)_3Si\ FG$,
wherein R is methyl or ethyl, and FG is independently chosen for each monomer from the group consisting of
linear, branched and cyclic alkyl residues of 1 to 20 carbons terminating in a 1-alkenyl ether;
linear, branched and cyclic alkyl ether residues of 1 to 20 carbons and 1 to 9 oxygens terminating in a 1-alkenyl ether;
linear, branched and cyclic alkyl residues of 1 to 20 carbons terminating in an acrylate, an alpha-chloroacrylate, an alpha-cyanoacrylate or a methacrylate;
linear, branched and cyclic alkyl ether residues of 1 to 20 carbons and 1 to 9 oxygens terminating in an acrylate, an alpha-chloroacrylate, an alpha-cyanoacrylate or a methacrylate;
linear, branched and cyclic alkyl residues of 1 to 20 carbons substituted with an epoxide;
linear, branched and cyclic alkyl ether residues of 1 to 20 carbons and 1 to 9 oxygens substituted with an epoxide;
arylalkyl residues of 1 to 20 carbons substituted with an epoxide;
arylalkyl ether residues of 1 to 20 carbons and 1 to 9 oxygens substituted with an epoxide; and
epoxy-functional organosiloxane residues of 1 to 20 silicons and 1 to 20 carbons;
with 0.5 to 2.5 equivalents of water in the presence of an ion exchange resin and separating the resin from said siloxane oligomer.

7. The process of claim 6, wherein said ion exchange resin is comprised of quaternary ammonium functionality.

8. The process of claim 6, wherein R is methyl or ethyl, and FG is independently chosen for each monomer from the group having structures A–P.

C 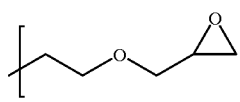

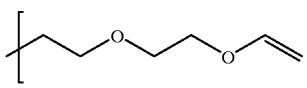

D 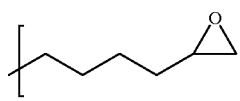

P 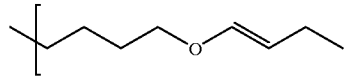

E 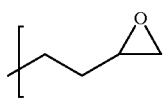

9. The process of claim 8, wherein said ion exchange resin is a quaternary ammonium resin.

10. A polymerizible siloxane oligomer produced by reacting one or more alkoxy silane monomers of formula $(RO)_3Si$ FG, wherein R is alkyl of 1–10 carbons and FG has a structure independently chosen for each monomer from the group consisting of:

F 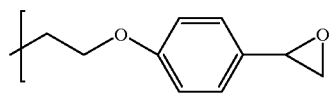

linear, branched and cyclic alkyl residues of 1 to 20 carbons terminating in a 1-alkenyl ether;

linear, branched and cyclic alkyl ether residues of 1 to 20 carbons and 1 to 9 oxygens terminating in a 1-alkenyl ether;

G 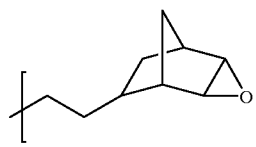

linear, branched and cyclic alkyl residues of 1 to 20 carbons terminating in an acrylate, an alpha-chloroacrylate, an alpha-cyanoacrylate or a methacrylate;

H 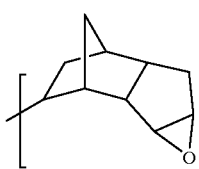

linear, branched and cyclic alkyl ether residues of 1 to 20 carbons and 1 to 9 oxygens terminating in an acrylate, an alpha-chloroacrylate, an alpha-cyanoacrylate or a methacrylate;

linear, branched and cyclic alkyl residues of 1 to 20 carbons substituted with an epoxide;

J 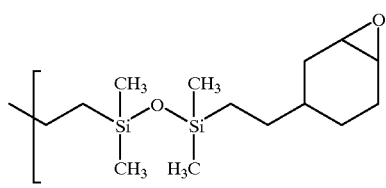

linear, branched and cyclic alkyl ether residues of 1 to 20 carbons and 1 to 9 oxygens substituted with an epoxide;

arylalkyl residues of 1 to 20 carbons substituted with an epoxide;

arylalkyl ether residues of 1 to 20 carbons and 1 to 9 oxygens substituted with an epoxide; and epoxy-functional organosiloxane residues of 1 to 20 silicons and 1 to 20 carbons;

K 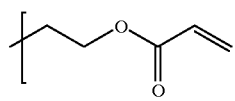

with 0.5 to 2.5 equivalents of water, in the presence of an ion exchange resin, optionally in the presence of a solvent, and separating the resin from said siloxane oligomer.

11. A polymerizible oligomer according to claim 10, such that said oligomer has a viscosity of between 100 and 1,000,000 cps.

L 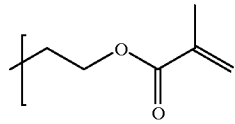

12. A polymerizible oligomer according to claim 10, such that said oligomer has a viscosity of greater than 1,000,000 cps.

13. A polymerizible siloxane oligomer according to claim 10, wherein FG has a structure independently chosen for each monomer from the group consisting of the structures of Formulae A–P.

M 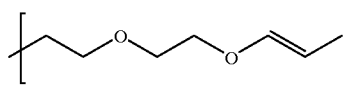

N 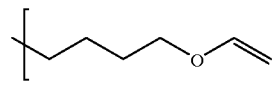

A 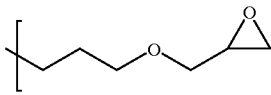

B 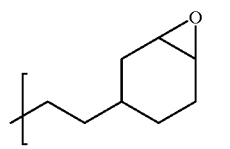

C 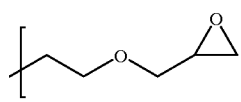

D 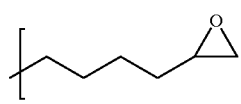

E 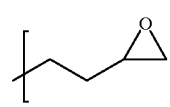

F 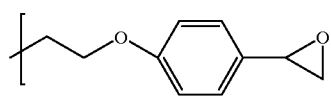

G 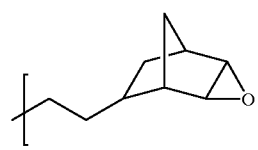

H 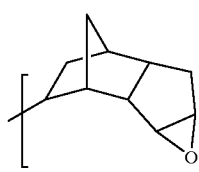

J 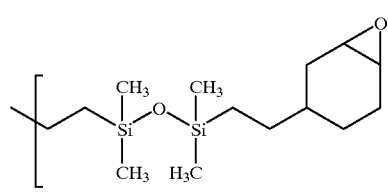

K 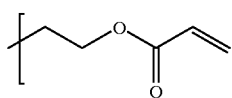

L 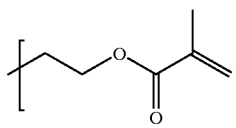

M 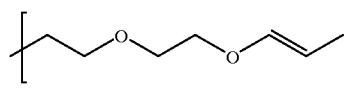

N 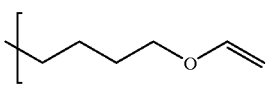

O 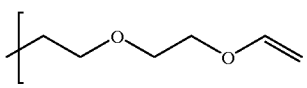

P 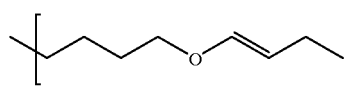

14. A polymerizible oligomer according to claim 13, wherein said oligomer has a viscosity of between 100 and 1,000,000 cps.

15. A polymerizible oligomer according to claim 13, wherein said oligomer has a viscosity of greater than 1,000,000 cps.

16. A polymerizible siloxane oligomer according to claim 10, wherein FG for each monomer is independently 2-(3,4-epoxycyclohexylethyl) or 3-glycidoxypropyl.

17. A polymerizible oligomer according to claim 16, wherein said oligomer has a viscosity of between 100 and 1,000,000 cps.

18. A polymerizible oligomer according to claim 16, wherein said oligomer has a viscosity of greater than 1,000,000 cps.

* * * * *